United States Patent [19]

Takemoto et al.

US005723165A

[11] Patent Number: 5,723,165
[45] Date of Patent: Mar. 3, 1998

[54] ASPARTYLDIPEPTIDE DERIVATIVES AND SWEETENER COMPOSITIONS CONTAINING THE SAME

[75] Inventors: Tadashi Takemoto; Yusuke Amino; Ryoichiro Nakamura, all of Kawasaki, Japan

[73] Assignee: Ajinomoto Co., Inc., Tokyo, Japan

[21] Appl. No.: 500,405

[22] Filed: Jul. 10, 1995

[30] Foreign Application Priority Data

| Jul. 8, 1994 | [JP] | Japan | 6-157503 |
| Oct. 7, 1994 | [JP] | Japan | 6-244235 |
| Jan. 31, 1995 | [JP] | Japan | 7-014241 |
| Mar. 2, 1995 | [JP] | Japan | 7-042818 |

[51] Int. Cl.$^6$ ................................................ C07K 5/072
[52] U.S. Cl. ................... 426/548; 562/450; 424/439; 530/801; 930/10; 930/21
[58] Field of Search ................... 426/548; 562/450; 424/439; 530/801; 930/10, 21, DIG. 555

[56] References Cited

U.S. PATENT DOCUMENTS 5,286,509  2/1994  D'Angelo et al. .................. 426/548

FOREIGN PATENT DOCUMENTS 0 034 876  9/1981  European Pat. Off. .
0 069 811  1/1983  European Pat. Off. .
0719789  3/1996  European Pat. Off. .
WO 94/00028  1/1994  WIPO .

OTHER PUBLICATIONS

Journal of Agricultural and Food Chemistry, vol. 39, No. 4, pp. 782–785, Apr. 1991, Guang–Zhi Zeng, et al., "In the Pursuit of a Better Sweetener".

Sweeny et al. (1995) J. Agric. Food Chem. vol. 43, pp. 1969–1976.

Primary Examiner—John Ulm
Assistant Examiner—Prema Mertz
Attorney, Agent, or Firm—Oblon, Spivak, McClelland, Maier & Neustadt, P.C.

[57] ABSTRACT

Aspartyldipeptide compounds of the formula (I)

$$L\text{-Asp-}X\text{-NH-}C^*R_1R_2 \qquad (I)$$

where $R_1$ is alkyl or alkoxymethyl, $R_2$ is phenyl, benzyl, cyclohexyl or cyclohexylmethyl, $C^*$ has an (S) configuration when $R_1$ is alkyl and an (R) configuration when $R_1$ is alkoxymethyl and X is a residue of a D-α-amino acid, a DL-α-amino acid or a residue of a cyclic or acyclic α,α-diallylamino acid and the bond between L-Asp and X is an α-bond; and their use as active ingredients in sweetener compositions.

17 Claims, No Drawings

ASPARTYLDIPEPTIDE DERIVATIVES AND SWEETENER COMPOSITIONS CONTAINING THE SAME

BACKGROUND OF THE INVENTION

1. Field of the Invention

The present invention relates to novel aspartyldipeptide derivatives and their salts and to sweetener compositions containing the derivative or its salt as the active ingredient.

2. Discussion of the Background

With advanced eating habits these days, obesity due to over-intake of sugar and its related various diseases have become significant problems. Thus, the development of low-calorie sweeteners useful as sugar substitutes is desired. At present, aspartame is one popular sweetener which is safe and has good taste. However, aspartame has a disadvantage in its heat stability, such as during cooking. One attempt to improve the stability and the sweetness potency of aspartame, has been to make amide derivatives of aspartyl-D-amino acid having no ester bond (for example, see the compounds described in U.S. Pat. Nos. 4,411,925 and 5,286,509).

SUMMARY OF THE INVENTION

Accordingly, one object of the present invention is to provide novel aspartyldipeptide amide derivatives and their salts which can be produced from readily available amino acid components and amine components.

A further object of the present invention is to provide aspartyldipeptide amide derivatives and salts which are highly stable and highly safe.

A further object of the present invention is to provide low-calorie sweeteners containing aspartyldipeptide amide derivatives and their salts as the active ingredients.

These and other objects of the present invention have been satisfied by the discovery of aspartyldipeptide amide derivatives of formula (1) L-Asp-X-NH-C*HR$_1$R$_2$ which are useful as sweeteners which are satisfactorily stable, sweet and safe.

DETAILED DESCRIPTION OF THE PREFERRED EMBODIMENTS

The present invention relates to aspartyldipeptide derivatives of the following for formula (I):

L-Asp-X-NH-C*HR$_1$R$_2$     (1)

wherein R$_1$ represents an alkyl group having from 1 to 6 carbon atoms, or an alkoxymethyl group having from 2 to 7 carbon atoms; R$_2$ represents a phenyl group, a benzyl group, a cyclohexyl group, or a cyclohexylmethyl group; the structure having the C* atom is of an (S) configuration when R$_1$ is an alkyl group but is of an (R) configuration when R$_1$ is an alkoxymethyl group; wherein when R$_1$ is an alkyl group, X represents a residue of a D-α-amino acid or DL-α-amino acid, such as D-norleucine, D-leucine, D-isoleucine, D-alloisoleucine, D-threonine, D-O-methylthreonine, D-allothreonine, D-O-methylallothreonine, D- or DL-furylglycine, etc., or a residue of a cyclic or acyclic α,α-dialkylamino acid having from 3 to 6 carbon atoms, but when R$_1$ is an alkoxymethyl group, X represents a residue of a D-α-amino acid or DL-α-amino acid, such as D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenylglycine, D- or DL-furylglycine, etc., or a residue of a cyclic or acyclic α,α-dialkylamino acid having from 3 to 6 carbon atoms, and the bond between L-Asp and X is an α-bond.

Suitable salts of the compounds of the present invention, include biologically acceptable salts which do not hinder the sweetening properties of the compound. Examples of such salts include salts with alkali metals such as sodium or potassium, salts with alkaline earth metals such as calcium or magnesium, salts with amines such as monoethanolamine, salts with inorganic acids such as hydrochloric acid or sulfuric acid, and salts with organic acids such as citric acid or acetic acid.

The aspartyldipeptide derivatives of the present invention can be produced according to conventional peptide synthesis methods (see Izumiya, et al., Bases and Experiments of Peptide Synthesis, published by Maruzen on Jan. 20, 1985). In particular, an α-amino acid, having the amino group protected, is condensed with the corresponding amine and thereafter the protective group is removed. Next, the thus-obtained amino acid amide is condensed with L-aspartic acid, having the β-carboxylic acid and the amino group protected, to give a dipeptidamide and thereafter the protective groups are removed to obtain the intended α-L-aspartyl-α-amino acid amide. Alternatively, L-aspartic acid, having the β-positioned carboxylic acid and the amino group protected, is esterified to be an active ester, then the ester is reacted with an α-amino acid and condensed with the corresponding amine. Finally, the protective groups are removed to obtain the intended α-L-aspartyl-α-amino acid amide.

β-alkoxyamines to be used for producing the compounds of the present invention can be readily obtained from amino acids in optically-active form according to known methods (see A. I. Meyers, at al., J. Org. Chem., 43, 892 (1978)).

N-benzyloxycarbonyl-DL-furylglycine to be used for producing the compounds of the present invention can be readily obtained according to known methods (see D. Ben-Ishai, et al., Tetrahedron, 31, 863 (1975); ibid., 32, 1571 (1976)). However, the above methods disclosed in the references are noted for illustrative purposes only and are not intended to be limiting.

Sensory evaluation of the sweetness of the compounds and their salts of the present invention has revealed that their taste is similar to that of sugar and their sweetness is strong. For example, the sweetness potency value of α-L-aspartyl-D-threonine(S)-α-ethylbenzylamide was about 1300 times that of sugar; that of α-L-aspartyl-DL-furylglycine (S)-α-ethylbenzylamide was about 1200 times that of sugar; that of α-L-aspartyl-α-aminocyclopentanecarboxylic acid (S)-α-ethylbenzylamide was about 1000 times that of sugar; that of α-L-aspartyl-α-aminocyclohexanecarboxylic acid (S)-α-ethylbenzylamide was about 1000 times that of sugar; that of α-L-aspartyl-D-α-aminobutyric acid (R)-α-methoxymethylbenzylamide was about 1200 times that of sugar; that of α-L-aspartyl-D-valine (R)-α-methoxymethylbenzylamide was about 1300 times that of sugar; and that of α-L-aspartyl-DL-furylglycine (R)-α-methoxymethylbenzylamide was about 1200 times that of sugar. The compounds of the present invention have been compared with α-L-aspartyl-D-α-aminobutyric acid (S)-α-ethylbenzylamide (comparative compound) which is known to have the highest degree of sweetness from among the aspartyldipeptide derivatives described in U.S. Pat. No. 5,286,509. From the sweetness potency values, one of ordinary skill in the art can readily prepare compositions using the compounds of the present invention having the desired level of sweetening ability.

With respect to stability in an acidic aqueous solution, the percentage (survival rate) of the compound still surviving in an acidic aqueous solution having a pH of 3 at 80° C. for 7 hours by HPLC was measured. For example, the survival rate of α-L-aspartyl-D-isoleucine (S)-α-ethylbenzylamine was about 9 times that of the comparative compound; that of α-L-aspartyl-α-aminocyclopentanecarboxylic acid (S)-α-ethylbenzylamide was about 10 times that of the comparative compound; and that of α-L-aspartyl-α-aminocyclohexanecarboxylic acid (S)-α-ethylbenzylamide was about 9 times that of the comparative compound.

Toxicity testing of the compounds of the present invention by oral administration of 2.0 g/kg of each compound once to ICR male mice showed no problematic toxicity for α-L-aspartyl-D-threonine (S)-α-ethylbenzylamlde, α-L-aspartyl-DL-furylglycine (S)-α-ethylbenzylamide, α-L-aspartyl-α-aminocyclohexanecarboxylic acid (S)-α-ethylbenzylamide, α-L-aspartyl-D-valine (R)-α-methoxymethylbenzylamide and α-L-aspartyl-DL-furylglycine (R)-α-methoxymethylbenzylamide, leading to the conclusion that all are safe from a toxicity standpoint.

The structures of some aspartyldipeptide derivatives of the present invention that have been produced herein are shown in Table I below, along with the results of the sensory evaluation of the compounds.

TABLE 1

Structures and Sweetness Potency Value of Aspartyldipeptide Derivatives

L-Asp-X-NH-C*HR$_1$R$_2$　　　(1)

| X | Configuration of C* | R1 | R2 | Sweetness[1] Potency |
|---|---|---|---|---|
| D-Leu | (S) | Et | Ph | 100 |
| D-Ile | (S) | Et | Ph | 500 |
| D-allo-Ile | (S) | Et | Ph | 90 |
| D-Thr | (S) | Et | Ph | 1300 |
| D-Thr(Me) | (S) | Et | Ph | 150 |
| DL-Fug[2] | (S) | Et | Ph | 1200 |
| AIB[3] | (S) | Et | Ph | 200 |
| DEG[4] | (S) | Et | Ph | 200 |
| DL-$^i$Val[5] | (S) | Et | Ph | 100 |
| AC5C[6] | (S) | Et | Ph | 1000 |
| AC6C[7] | (S) | Et | Ph | 1000 |
| D-Ala | (R) | CH$_2$OMe | Ph | 300 |
| D-Abu[8] | (R) | CH$_2$OMe | Ph | 1200 |
| D-Ile | (R) | CH$_2$OMe | Ph | 500 |
| D-Phg[9] | (R) | CH$_2$OMe | Ph | 500 |
| AC6C[7] | (R) | CH$_2$OMe | Ph | 250 |
| D-Thr | (R) | CH$_2$OMe | Ph | 500 |
| DL-Fug[2] | (R) | CH$_2$OMe | Ph | 1200 |
| D-Val | (R) | CH$_2$OMe | Ph | 1300 |
| D-Val | (R) | CH$_2$OEt | Ph | 500 |
| D-Val | (S) | CH$_2$OMe | Ph | <20 |
| D-Val | (R) | CH$_2$OMe | $^i$Pr | 30 |
| D-Val | (S) | CH$_2$OMe | $^i$Pr | 40 |

[1]based on an aqueous solution of 4% sucrose having a sweetness potency of 1 (one);
[2]Fug = furylglycine;
[3]AIB = α-aminoisobutyric acid;
[4]DEG = α,α-diethylglycine;
[5]$^i$Val = isovaline;
[6]AC5C = α-aminocyclopentanecarboxylic acid
[7]AC6C = α-aminocyclohexanecarboxylic acid
[8]Abu = α-aminobutyric acid
[9]Phg = phenylglycine When the compounds or their salts of the present invention are used as sweeteners, they may be combined with one another or with any other sweeteners, as a matter of course, unless such combination detracts from the advantages of the present invention. The sweetener compositions of the present invention may also contain one or more conventional biologically acceptable excipients or additives, so long as they have no adverse affect on the taste of the composition.

Having generally described this invention, a further understanding can be obtained by reference to certain specific examples which are provided herein for purposes of illustration only and are not intended to be limiting unless otherwise specified.

EXAMPLE 1

Production of α-L-aspartyl-D-threonine (S)-α-ethylbenzylamide:

To a solution of 2.50 g (8.1 of mmols) of N-t-butoxycarbonyl-O-benzyl-D-threonine and 1.31 g (9.7 mmols) of (S)-α-ethylbenzylamine in 50 ml of methylene chloride were added 1.55 g (8.1 mmols) of water-soluble carbodiimide hydrochloride and 1.09 g (8.1 mmols) of HOBt (1-hydroxy benzotriazole hydrate) under cooling, and the mixture was stirred for one hour under cooling and then overnight at room temperature. The reaction mixture was concentrated under reduced pressure, and 100 ml of ethyl acetate were added. The resulting residue was washed two times each with 50 ml of aqueous 5% citric acid, once with 50 ml of water, two times each with 50 ml of aqueous 5% sodium hydrogencarbonate and once with 50 ml of brine, in that order. The resulting organic layer was dried with anhydrous magnesium sulfate, the magnesium sulfate was removed by filtration, and the resulting filtrate was concentrated under reduced pressure to obtain 3.45 g (8.1 mmols) of a solid product of N-t-butoxycarbonyl-O-benzyl-D-threonine (S)-α-ethylbenzylamide.

To a solution of 3.41 g (8.0 mmols) of N-t-butoxycarbonyl-O-benzyl-D-threonine (S)-α-ethylbenzylamide in 35 ml of methylene chloride was added 120 ml of formic acid and the mixture was stirred at room temperature for 5 hours. The reaction mixture was concentrated under reduced pressure, and 50 ml of ethyl acetate was added. The resulting residue was washed with 50 ml of aqueous saturated sodium hydrogencarbonate. The resulting organic layer was dried with anhydrous magnesium sulfate, the magnesium sulfate was removed by filtration, and the resulting filtrate was concentrated under reduced pressure.

The resulting residue was dissolved in 80 ml of methylene chloride, and 3.16 g (8.9 mmols) of β-benzyl N-benzyloxycarbonyl-L-aspartate was added thereto. 1.70 g (8.9 mmols) of water-soluble carbodiimide hydrochloride and 1.20 g (8.9 mmols) of HOBt were added thereto under cooling and stirred for one hour under cooling and then overnight at room temperature. The reaction mixture was concentrated under reduced pressure, and 100 ml of ethyl acetate was added. The resulting residue was washed two times each with 50 ml of aqueous 5% citric acid, once with 50 ml of water, two times each with 50 ml of aqueous 5% sodium hydrogencarbonate and once with 50 ml of brine, in that order. The resulting organic layer was dried with anhydrous magnesium sulfate, the magnesium sulfate was removed by filtration, and the resulting filtrate was concentrated under reduced pressure to obtain 5.30 g (8.0 mmols) of a solid product of N-benzyloxycarbonyl-β-benzyl-L-aspartyl-O-benzyl-D-threonine-(S)-α-ethylbenzylamide.

To a solution of 5.30 g (8.0 mmols) of N-benzyloxycarbonyl-β-benzyl-L-aspartyl-O-benzyl-D-threonine (S)-α-ethylbenzylamide in 150 ml of methanol were added 1.0 ml of acetic acid and 3.0 g of 5% Pd-carbon (water content 50%), and the mixture was reduced under hydrogen overnight at room temperature and then at 50° C. for 3 hours. The catalyst was removed by filtration, the resulting filtrate was concentrated under reduced pressure, and the residue was crystallized from water to obtain 1.60 g (4.6 mmols) of α-L-aspartyl-D-threonine (S)-α-ethylbenzylamide.

$^1$HNMR(DMSO-$d_6$) δ:0.84 (t, 3H), 1.06 (d, 3H), 1.69 (quint, 2H), 2.32 (dd, 1H), 2.54 (dd, 1H), 3.83 (dd, 1H), 4.03 (dq, 1H), 4.19 (brs, 1H), 4.70 (dd, 1H), 7.18–7.35 (m, 5H), 8.17 (d, 1H), 8.59 (brd, 1H).

FAB-MS 352 (MH$^+$)

The sweetness potency of the compound was 1300 times that of sugar.

EXAMPLE 2

Production of α-L-aspartyl-D-threonine (R)-α-methoxymethylbenzylamide:

The same process as in Example 1 was repeated, except that (R)-α-methoxymethylbenzylamine was used in place of (S)-α-ethylbenzylamine, and α-L-aspartyl-D-threonine (R)-α-methoxymethylbenzylamide was obtained as a solid product. The total yield was 75.3%.

$^1$HNMR (DMSO-$d_6$) δ:1.07 (d, 3H), 2.32 (dd, 1H), 2.56 (dd, 1H), 3.24 (S, 3H), 3.47–3.56 (2dd, 2H), 3.87 (dd, 1H), 3.96–4.04 (m, 1H), 4.21 (brs, 1H), 5.03 (dd, 1H), 7.22–7.38 (m, 5H), 8.32 (d, 1H), 8.66 (brd, 1H).

FAB-MS 368 (MH$^+$)

The sweetness potency of the compound was 500 times that of sugar.

EXAMPLE 3

Production of α-L-aspartyl-D-isoleucine (S)-α-ethylbenzylamide:

To a mixture comprised of 5.08 g (14.2 mmols) of β-benzyl N-benzyloxycarbonyl-L-aspartate, 1.64 g (14.2 mmols) of HOSu (N-hydroxy succinic acid) and 90 ml of tetrahydrofuran was added 2.94 g (14.2 mmols) of dicyclohexycarbodiimide under cooling, and the mixture was stirred for one hour under cooling and then overnight at room temperature. The reaction mixture was filtered and the resulting filtrate was concentrated under reduced pressure. The residue was dissolved in 100 ml of dioxane, to which was added a solution that had been prepared by dissolving 2.20 g (16.8 mmols) of D-isoleucine and 1.9 ml (13 mmols) of triethylamine in 10 ml of dioxane and 20 ml of water. These were stirred overnight at room temperature. The reaction mixture was concentrated under reduced pressure, and 80 ml of water was added thereto. The separated aqueous layer was made acidic by adding aqueous 10% citric acid, and this was extracted two times each with 50 ml of ethyl acetate. The organic layer was washed with 50 ml of water and then with 50 ml of brine. This was dried with anhydrous magnesium sulfate, the magnesium sulfate was removed by filtration, and the resulting filtrate was concentrated under reduced pressure to obtain 6.69 g (14.2 mmols) of syrup-like N-benzyloxycarbonyl-β-benzyl-L-aspartyl-D-isoleucine.

To a solution of 6.69 g (14.2 mmols) of N-benzyloxycarbonyl-β-benzyl-L-aspartyl-D-isoleucine and 2.04 g (15.1 mmols) of (S)-α-ethylbenzylamine in 200 ml of methylene chloride were added 2.73 g (14.2 mmols) of water-soluble carbodiimide hydrochloride and 1.92 g (14.2 mmols) of HOBt under cooling and stirred for one hour under cooling and then overnight at room temperature.

The reaction mixture was concentrated under reduced pressure, and 150 ml of ethyl acetate was added. The resulting residue was washed two times each with 70 ml of aqueous 5% citric acid, once with 70 ml of water, two times each with 70 ml of aqueous 5% sodium hydrogencarbonate and once with 70 ml of brine in that order. The resulting organic layer was dried with anhydrous magnesium sulfate, the magnesium sulfate was removed by filtration, and the resulting filtrate was concentrated under reduced pressure. The resulting residue was dissolved in chloroform and concentrated under reduced pressure. The resulting solid residue was washed with ethyl acetate and dried to obtain 2.81 g (4.7 mmols) of N-benzyloxycarbonyl-β-benzyl-L-aspartyl-D-isoleucine (S)-α-ethylbenzylamide.

To a suspension of 2.81 g (4.7 mmols) of N-benzyloxycarbonyl-β-benzyl-L-aspartyl-D-isoleucine (S)-α-ethylbenzylamide in 150 ml of methanol and 50 ml of water was added 2.0 g of 10% Pd-carbon (water content 50%). The mixture was reduced under hydrogen at room temperature for 5 hours. The catalyst was removed by filtration, and the resulting filtrate was concentrated under reduced pressure to be 20 ml. The crystals thus precipitated were taken out by filtration and dried to obtain 1.22 g (3.4 mmols) of α-L-aspartyl-D-isoleucine (S)-α-ethylbenzylamide.

$^1$HNMR (DMSO-$d_6$) δ:0.82 (t, 3H), 0.84 (t, 3H), 0.86 (d, 3H), 1.03–1.18 (m, 1H), 1.34–1.47 (m, 1H), 1.63–1.85 (m, 3H), 2.86 (d, 2H), 4.07–4.17 (m, 1H), 4.34 (dd, 1H), 4.70 (dd, 1H), 7.19–7.36 (m, 5H), 8.27 (brd, 2H), 8.56 (d, 1H), 8.62 (d, 1H).

FAB-MS 364 (MH$^+$)

The sweetness potency of the compound was 500 times that of sugar. The stability (in terms of the survival rate in an acidic aqueous solution) was about 9 times that of α-L-aspartyl-D-α-aminobutyric acid (S)-α-ethylbenzylamide.

EXAMPLE 4

Production of α-L-aspartyl-DL-furylglycine (S)-α-ethylbenzylamide:

To a solution of 2.20 g (8.0 mmols) of N-benzyloxycarbonyl-DL-furylglycine and 1.08 g (8.0 mmols) of (S)-α-ethylbenzylamine in 30 ml of methylene chloride were added 1.69 g (8.8 mmols) of water-soluble carbodiimide hydrochloride and 1.19 g (8.8 mmols) of HOBt under cooling, and the mixture was stirred for one hour under cooling and then overnight at room temperature. The reaction mixture was concentrated under reduced pressure, and 100 ml of ethyl acetate were added. The resulting residue was washed two times each with 50 ml of aqueous 5% citric acid, once with 50 ml of water, two times each with 50 ml of aqueous 5% sodium hydrogencarbonate and once with 50 ml of brine, in that order. The resulting organic layer was dried with anhydrous magnesium sulfate, the magnesium sulfate was removed by filtration, and the resulting filtrate was concentrated under reduced pressure. This was recrystallized from ethyl acetate-hexane to obtain 2.81 g (7.2 mmols) of N-benzyloxycarbonyl-DL-furylglycine (S)-α-ethylbenzylamide.

To a solution of 2.33 (5.9 mmols) of N-benzyloxycarbonyl-DL-furylglycine (S)-α-ethylbenzylamide in 50 ml of methanol were added 590 mg of 5% Pd-carbon (water content 50%) and 30 mg of quinoline. The mixture was reduced under hydrogen at room temperature for 1.5 hours. The catalyst was removed by filtration, the resulting filtrate was concentrated under reduced pressure, and the residue was dissolved in 100 ml of chloroform. The organic layer was washed with 50 ml of aqueous 5% sodium hydrogencarbonate and then with 50 ml of brine. Next, this was dried with anhydrous magnesium sulfate, the magnesium sulfate was removed by filtration, and the resulting filtrate was concentrated under reduced pressure.

The residue was dissolved in 50 ml of methylene chloride, and 2.33 g (6.5 mmols) of β-benzyl N-benzyloxycarbonyl-L-aspartate was added thereto. Next, 1.25 g (6.3 mmols) of water-soluble carbodiimide hydrochloride and 0.88 g (6.5 mmols) of HOBt were added thereto under cooling and stirred for one hour under cooling and then overnight at room temperature. The reaction mixture was concentrated under reduced pressure, and 150 ml of ethyl acetate was added. The residue was washed two times each with 50 ml of aqueous 5% citric acid, once with 50 ml of water, two times each with 50 ml of aqueous 5% sodium hydrogencarbonate and once with 50 ml of brine, in that order. The resulting organic layer was dried with magnesium sulfate, the magnesium sulfate was removed by filtration, the resulting filtrate was concentrated under reduced pressure, and the residue was recrystallized from ethyl acetate-hexane to obtain quantitatively N-benzyloxycarbonyl-β-benzyl-L-aspartyl-DL-furylglycine-(S)-α-ethylbenzylamide.

To a suspension of 3.64 g (6.1 mmols) of N-benzyloxycarbonyl-β-benzyl-L-aspartyl-DL-furylglycine (S)-α-ethylbenzylamide in 50 ml of methanol was added 630 mg of 5% Pd-carbon (water content 50%) and 34 mg of quinoline. The mixture was reduced under hydrogen at room temperature for 1.5 hours. The catalyst was removed by filtration, and the methanol was removed under reduced pressure. 200 ml of water was added to the residue and the crystal formed was separated from the mother liquid by filtration. The both were well washed with diethyl ether and ethyl acetate. The crystal was dissolved in 100 ml of methanol and combined with the mother liquid. This was concentrated under reduced pressure to about ⅒, and the crystal thus precipitated was taken out by filtration and dried to obtain 1.67 g (4.5 mmols) of α-L-aspartyl-DL-furylglycine (S)-α-ethylbenzylamide.

$^1$HNMR (DMSO-d$_6$) δ:0.77 (t, J=6.9 Hz, 1.5H) , 0.85 (t, J=7, 4z, 1.5H), 1.60–1.75 (m, 2H), 2.19–2.33 (m, 1H), 2.41–2.57 (m, 1H), 3.65–3.80 (m, 1H), 4.63–4.72 (m, 1H), 5.61 (s, 1H), 6.22–6.44 (m, 2H), 7.19–7.40 (m, 5H), 7.59 (m, 0.5H), 7.64 (m, 0.5H), 8.72 (d, J=9.1 Hz, 0.5H), 8.76 (d, J=9.3 Hz, 0.5H), 8.95 (brs, 1H).

FAB-MS 374 (MH$^+$)

The sweetness potency of the compound was 1200 times that of sugar.

EXAMPLE 5

Production of α-L-aspartyl-DL-furylglycine (R)-α-methoxymethylbenzylamide:

The same process as in Example 4 was repeated, except that (R)-α-methoxymethylbenzylamine was used in place of (S)-α-ethylbenzylamine, and α-L-aspartyl-DL-furylglycine (R)-α-methoxymethylbenzylamide was obtained as a solid product. The total yield was 60.7%.

$^1$HNMR (DMSO-d$_6$) δ: 2.21–2.34 (m, 1H), 2.42–2.57 (m, 1H), 3.22 (s, 1.5H), 3.26 (s, 1.5H), 3.46–3.60 (m, 2H), 3.69–3.80 (m, 1H), 4.98–5.07 (m, 1H), 5.65 (s, 1H), 6.27–6.45 (m, 2H), 7.18–7.40 (m, 5H), 7.59 (m, 0.5H), 7.64 (m, 0.5H), 8.87 (d, J=8.3 Hz, 0.5H), 8.96 (d, J=8.1 Hz, 0.5H), 9.10 (brs, 1H).

FAB-MS 390 (MH$^+$).

The sweetness potency of the compound was 1200 times that of sugar.

EXAMPLE 6

Production of α-L-aspartyl-α-aminocyclopentanecarboxylic acid (S)-α-ethylbenzylamide:

To a solution of 1.15 g (5.0 mmols) of N-t-butoxycarbonyl-α-aminocyclopentanecarboxylic acid and 0.68 g (5.0 mmols) of (S)-α-ethylbenzylamine in 35 ml of methylene chloride were added 0.96 g (5.5 mmols) of water-soluble carbodiimide hydrochloride and 0.68 g (5.0 mmols) of HOBt under cooling, and the mixture was stirred for one hour under cooling and then overnight at room temperature. The reaction mixture was concentrated under reduced pressure, and 50 ml of aqueous 5% citric acid was added. The resulting residue was extracted two times each with 50 ml of ethyl acetate and then washed with 20 ml of water, 25 ml of aqueous 5% sodium hydrogencarbonate and 20 ml of brine, in that order. The organic layer was dried with anhydrous magnesium sulfate and filtered, and the resulting filtrate was concentrated under reduced pressure to obtain 1.63 g (4.7 mmols) of a solid product of N-t-butoxycarbonyl-α-aminocyclopentanecarboxylic acid (S)-α-ethylbenzylamide.

13 ml of 4N-HCl/dioxane solution was added to 0.87 g (2.5 mmols) of N-t-butoxycarbony-α-aminocyclopentanecarboxylic acid (S)-α-ethylbenzylamide, and the mixture was stirred at room temperature for one hour. The reaction mixture was concentrated under reduced pressure. 30 ml of ether was added to the residue, and this was again concentrated. The residue was dissolved in 30 ml of methylene chloride and 0.39 ml (2.75 mmols) of triethylamine, and 0.98 g (2.5 mmols) of β-benzyl-N-benzyloxycarbonyl-L-aspartate were added thereto. Under cooling, 0.53 g (2.75 mmols) of water-soluble carbodiimide hydrochloride and 0.34 g (2.5 mmols) of HOBt were added thereto, and the mixture was stirred for one hour under cooling and then overnight at room temperature. The reaction mixture was concentrated under reduced pressure, 50 ml of aqueous 5% citric acid was added to the residue, which was extracted two times each with 50 ml of ethyl acetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure. The residue was dissolved in 30 ml of methanol, 0.25 g of 10% Pd-carbon (water content 50%) was added thereto, and the mixture was reduced under hydrogen. 40 ml of water was added to this, the catalyst was removed by filtration, and the resulting filtrate was concentrated to about ¼. This was then stored in a refrigerator overnight. The crystal thus precipitated was removed by filtration and dried to obtain 0.64 g (1.77 mmols) of α-L-aspartyl-α-aminocyclopentanecarboxylic acid (S)-α-ethylbenzylamide.

$^1$HNMR (DMSO-d$_6$) δ:0.83 (t, 3H), 1.55–1.78 (t, 6H), 1.85–2.08 (m, 4H), 2.44 (dd, 1H), 2.66 (dd, 1H), 3.82 (brt, 1H), 4.67 (brq, 1H), 7.15–7.22 (m, 1H), 7.22–7.35 (m, 4H), 7.87 (d, 1H), 8.51 (brs, 1H).

FAB-MS 362 (MH$^+$)

The sweetness potency of the compound was 1000 times that of sugar. The stability (in terms of the survival rate in an acidic aqueous solution) was about 10 times that of α-L-aspartyl-D-α-aminobutyric acid (S)-α-ethylbenzylamide.

EXAMPLE 7

Production of α-L-aspartyl-α-aminocyclohexanecarboxylic acid (S)-α-ethylbenzylamide:

To a solution of 1.22 g (5.0 mmols) of N-t-butoxycarbonyl-α-aminocyclohexanecarboxylic acid and 0.68 g (5.0 mmols) of (S)-α-ethylbenzylamine in 35 ml of methylene chloride were added 0.96 g (5.5 mmols) of water-soluble carbodiimide hydrochloride and 0.68 g (5.0 mmols) of HOBt under cooling, and the mixture was stirred for one hour under cooling and then overnight at room temperature. The reaction mixture was concentrated under reduced pressure, and 50 ml of aqueous 5% citric acid was added. The resulting residue was extracted two times each with 50 ml of ethyl acetate and then washed with 20 ml of water, 25 ml of aqueous 5% sodium hydrogencarbonate and 20 ml of brine, in that order. The organic layer was dried with anhydrous magnesium sulfate and filtered, and the resulting filtrate was concentrated under reduced pressure to obtain 1.66 g (4.6 mmols) of a solid product of N-t-butoxycarbonyl-α-aminocyclohexanecarboxylic acid (S)-α-ethylbenzylamide.

13 ml of 4N-HCl/dioxane solution was added to 0.68 g (1.88 mmols) of N-t-butoxycarbonyl-α-aminocyclohexanecarboxylic acid (S)-α-ethylbenzylamide, and the mixture was stirred at room temperature for one hour. The reaction mixture was concentrated under reduced pressure, 30 ml of ether was added to the residue, and this was again concentrated. The residue was dissolved in 30 ml of methylene chloride, and 0.29 ml (2-07 mmols) of triethylamine, and 0.74 g (2.07 mmols) of β-benzyl N-benzyloxycarbonyl-L-aspartate were added thereto. While cooling, 0.40 g (2.07 mmols) of water-soluble carbodiimide hydrochloride and 0.25 g (1.88 mmols) of HOBt were added thereto, and the mixture was stirred for one hour under cooling and then overnight at room temperature. The reaction mixture was concentrated under reduced pressure, 50 ml of aqueous 5% citric acid was added to the residue, which was extracted two times each with 50 ml of ethylacetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure. The residue was dissolved in 30 ml of methanol, 0.25 g of 10% Pd-carbon (water content 50%) was added thereto, and the mixture was reduced under hydrogen. 40 ml of water was added to this, the catalyst was removed by filtration, and the resulting filtrate was concentrated to about ¼. This was then stored in a refrigerator overnight. The crystal thus precipitated was removed by filtration and dried to obtain 0.40 g (1.07 mmols) of α-L-aspartyl-α-aminocyclohexanecarboxylic acid (S)-α-ethylbenzylamide.

$^1$HNMR (DMSO-d$_6$) δ:0.83 (T, 3H), 1.10–1.27 (m.1H), 1.33–1.78 (m, 9H), 1.93–2.13 (m.2H), 2.45 (dd, 1H), 2.65 (dd, 1H), 3.90–3.98 (m, 1H), 4.65 (brq, 1H), 7.15–7.22 (m, 1H), 7.22–7.30 (m.4H), 7.78 (brd. 1H), 8.25 (brs, 1H).

FAB-MS 376 (MH$^+$)

The sweetness potency of the compound was 1000 times that of sugar. The stability (in terms of the survival rate in an acidic aqueous solution) was about 9 times that of α-L-aspartyl-D-α-aminobutyric acid (S)-α-ethylbenzylamide.

EXAMPLE 8

Production of α-L-aspartyl-α-aminoisobutyric acid (S)-α-ethylbenzylamide:

To a solution of 1.02 g (5.0 mmols) of N-t-butoxycarbonyl-α-aminoisobutyric acid and 0.68 g (5.0 mmols) of (S)-α-ethylbenzylamine in 35 ml of methylene chloride were added 0.96 g (5.5 mmols) of water-soluble carbodiimide hydrochloride and 0.68 g (5.0 mmols) of HOBT under cooling, and the mixture was stirred for one hour under cooling and then overnight at room temperature. The reaction mixture was concentrated under reduced pressure, and 50 ml of aqueous 5% citric acid was added to the resulting residue, which was extracted two times each with 50 ml of ethyl acetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure to obtain 1.55 g (4.83 mmols) of a solid product of N-t-butoxycarbonyl-α-aminoisobutyric acid (S)-α-ethylbenzylamide.

25 ml of 4N-HCl/dioxane solution was added to 1.55 g (4.83 mmols) of N-t-butoxycarbonyl-α-aminoisobutyric acid (S)-α-ethylbenzylamide, and the mixture was stirred at room temperature for one hour. The reaction mixture was concentrated under reduced pressure, 30 ml of ether was added to the residue, and this was again concentrated. The residue was dissolved in 30 ml of methylene chloride, and 0.74 ml (5.28 mmols) of triethylamine and 1.71 g (5.28 mmols) of β-benzyl-N-t-butoxycarbonyl-L-aspartate were added thereto. Under cooling, 1.01 g (5.28 mmols) of water-soluble carbodiimide hydrochloride and 0.65 g (4.80 mmols) of HOBt were added thereto, and the mixture was stirred for one hour under cooling and then overnight at room temperature. The reaction mixture was concentrated under reduced pressure, 50 ml of aqueous 5% citric acid was added to the residue, which was extracted two times each with 50 ml of ethyl acetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure. 20 ml of 4N-HCl/dioxane solution was added to the residue and stirred for 30 minutes at room temperature. The reaction mixture was concentrated under reduced pressure, 30 ml of methanol was added thereto, and this was further concentrated.

The residue was dissolved in 30 ml of methanol, 0.40 g of 10% Pd-carbon (water content 50%) was added thereto, and the mixture was reduced under hydrogen. 40 ml of water was added to this, the catalyst was removed by filtration, and the resulting filtrate was concentrated under reduced pressure. The residue was dissolved in 50 ml of water and passed through 80 ml of an adsorption resin (SP207). Afterwards, the resin was washed with 300 ml of water. This was subjected to elution with 300 ml of water/methanol (1/1). The resulting eluate was concentrated under reduced pressure, and the residue was crystallized in ethanol. The crystal thus precipitated was removed by filtration and dried to obtain 0.87 g (2.60 mmols) of α-L-aspartyl-α-aminoisobutyric acid (S)-α-ethylbenzylamide.

$^1$HNMR(DMSO-d$_6$) δ:0.82 (t, 3H), 1.3 8 (d, 6H), 1.60–1.75 (m, 2H) 2.29 (dd, 1H), 2.50 (m, 1H) 3.58 (brt, 1H), 4.63 (q, 1H), 7.12–7.20 (m, 1H), 7.20–7.33 (m, 4H), 8.07 (d, 1H), 8.48 (brs, 1H).

FAB-MS 336 (MH$^+$)

The sweetness potency of the compound was 200 times that of sugar. The stability (in terms of the survival rate in an acidic aqueous solution) was about 2.6 times that of α-L-aspartyl-D-α-aminobutyric acid (S)-α-ethylbenzylamide.

EXAMPLE 9

Production of α-L-aspartyl-α-α-diethylglycine (S)-α-ethylbenzylamide:

To a solution of 1.99 g (8.6 mmols) of N-t-butoxycarbonyl-α,α-diethylglycine and 1.16 g (8.6 mmols) of (S)-α-ethylbenzylamine in 40 ml of methylene chloride were added 1.81 g (9.5 mmols) of water-soluble carbodiimide hydrochloride and 1.16 g (8.6 mmols) of HOBt under cooling, and the mixture was stirred for one hour under cooling and then overnight at room temperature. The reaction mixture was concentrated under reduced pressure, and 50 ml of aqueous 5% citric acid was added to the resulting residue, which was extracted two times each with 50 ml of ethyl acetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure to obtain 1.31 g (3.76 mmols) of a solid product of N-t-butoxycarbonyl-α,α-diethylglycine-(S)-α-ethylbenzylamide.

19 ml of 4N-HCl/dioxane solution were added to 1.31 g (3.76 mmols) of N-t-butoxycarbonyl-α,α-diethylglycine (S)-α-ethylbenzylamide, and the mixture was stirred at room temperature for one hour. The reaction mixture was concentrated under reduced pressure, 30 ml of ether was added to the residue, and this was again concentrated. The residue was dissolved in 25 ml of methylene chloride, and 0.55 ml (4.13 mmols) of triethylamine and 1.48 g (4.13 mmols) of β-benzyl-N-benzyloxycarbonyl-L-aspartate were added thereto. Under cooling, 0.79 g (4.13 mmols) of water-soluble carbodiimide hydrochloride and 0.51 g (3.76 mmols) of HOBt were added thereto, and these were stirred for one hour under cooling and then overnight at room temperature. The reaction mixture was concentrated under reduced pressure and 50 ml of aqueous 5% citric acid were added. The resulting residue was extracted two times each with 50 ml of ethyl acetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure. The residue was dissolved in 30 ml of methanol, 0.30 g of 10% Pd-carbon (water content 50) was added thereto, and the mixture was reduced under hydrogen. 40 ml of water was added to this, the catalyst was removed by filtration, and the resulting filtrate was concentrated to about ¼. This was then stored in a refrigerator overnight. The crystal thus precipitated was removed by filtration and dried to obtain 0.40 g (1.10 mmols) of α-L-aspartyl-α,α-diethylglycine (S)-α-ethylbenzylamide.

$^1$HNMR (DMSO-$d_6$) δ:0.46 (t, 3H), 0.65 (t, 3H), 0.87 (t, 3H), 1.60–1.92 (m, 4H), 2.12–2.30 (m, 2H), 2.43 (dd, 1H), 2.54 (m, 1H), 3.77 (brt, 1H), 4.69 (brq, 1H), 7.15–7.22 (m, 1H), 7.22–7.35 (m, 4H), 8.20 (d, 1H), 8.22 (brs, 1H).

FAB-MS 364 (MH$^+$)

The sweetness potency of the compound was 1000 times that of sugar. Regarding the stability, the compound did not decompose.

EXAMPLE 10

Production of α-L-aspartyl-DL-isovaline (S)-α-ethylbenzylamide:

To a solution of 0.50 g (2.3 mmols) of N-t-butoxycarbonyl-DL-isovaline and 0.31 g (2.3 mmols) of (S)-α-ethylbenzylamine in 50 ml of methylene chloride was added 0.44 g (2.3 mmols) of water-soluble carbodiimide hydrochloride under cooling, and the mixture was stirred for one hour under cooling and then overnight at room temperature. The reaction mixture was concentrated under reduced pressure, and 40 ml of aqueous 5% citric acid were added. The resulting residue was extracted two times each with 30 ml of ethyl acetate and then washed with 20 ml of water, 20 ml of aqueous 5% sodium hydrogencarbonate and 15 ml of brine, in that order. The resulting organic layer was dried with anhydrous magnesium sulfate and filtered, and the resulting filtrate was concentrated under reduced pressure to obtain 0.68 g (2.03 mmols) of a solid product of N-t-butoxycarbonyl-DL-isovaline (S)-α-ethylbenzylamide.

10 ml of 4N-HCl/dioxane solution was added to 0.66 (1.97 mmols) of N-t-butoxycarbonyl-DL-isovaline (S)-α-ethylbenzylamide, and the mixture was stirred at room temperature for one hour. The reaction mixture was concentrated under reduced pressure, 30 ml of ether were added to the residue, and this was again concentrated. The residue was dissolved in 20 ml of methylene chloride and 0.24 ml (1.76 mmols) of triethylamine and 0.63 g (1.76 mmols) of β-benzyl N-benzyloxycarbonyl-L-aspartate were added thereto. Under cooling, 0.34 g (1.76 mmols) of water-soluble carbodiimide hydrochloride was added thereto, and these were stirred for one hour under cooling and then overnight at room temperature. The reaction mixture was concentrated under reduced pressure, 50 ml of aqueous 5% citric acid were added to the residue, which was extracted two times each with 40 ml of ethyl acetate and then washed with 20 ml of water, 25 ml of aqueous 5% sodium hydrogencarbonate and 20 ml of brine, in that order. The resulting organic layer was dried with anhydrous magnesium sulfate and filtered, and the resulting filtrate was concentrated under reduced pressure. The residue was dissolved in 20 ml of methanol, 0.10 g of 10% Pd-carbon (water content 50%) was added thereto, and the mixture was reduced under hydrogen. 20 ml of water was added to this, the catalyst was removed by filtration, and the resulting filtrate was concentrated to about ⅕. This was then stored in a refrigerator overnight. The crystal thus precipitated was removed by filtration and dried to obtain 0.21 g of α-L-aspartyl-DL-isovaline (S)-α-ethylbenzylamide.

$^1$HNMR (DMSO-$d_6$) δ:0.69, 0.70 (t×2, 3H), 0.86 (t, 3H), 1.40, 1.41 (s×2, 3H), 1.66–1.96 (m, 4H), 2.72–2.85 (m, 1H), 2.92 (dd, 1H), 4.17 (t, 1H), 4.63–4.72 (m, 1H), 7.13–7.35 (m, 7H), 7.95, 8.07 (d×2, 1H), 8.31, 8.37 (s×2, 1H), 8.48 (brs, 1H), 8.22 (brs, 1H).

FAB-MS 350 (MH$^+$)

The sweetness potency of the compound was 100 times that of sugar. The stability (in terms of the survival rate in an acidic aqueous solution) was about 18 times that of α-L-aspartyl-D-α-aminobutyric acid (S)-α-ethylbenzylamide.

EXAMPLE 11

Production of α-L-aspartyl-D-valine (R)-α-methoxymethylbenzylamide:

60 ml of 4N-HCl/dioxane solution was added to 4.02 g (16.0 mmols) of N-t-butoxycarbonyl-(R)-α-methoxymethylbenzylamine, and the mixture was stirred at room temperature for one hour. The reaction mixture was concentrated under reduced pressure. 30 ml of ether were added to the residue, and this was further concentrated to obtain (R)-α-methoxymethylbenzylamine hydrochloride in quantitative yield.

The thus-obtained (R)-α-methoxymethylbenzylamine hydrochloride and 3.37 g (15.5 mmols) of N-t- butoxycarbonyl-D-valine were dissolved in 50 ml of methylene chloride, 2.67 g (16.5 mmols) of water-soluble carbodiimide hydrochloride, 2.23 g (16.5 mmols) of HOBt and 2.63 ml (17.5 mmols) of triethylamine were added thereto under cooling, and these were stirred for one hour under cooling and then overnight at room temperature. The reaction mixture was concentrated under reduced pressure, and 150 ml of ethyl acetate were added. The resulting residue was washed two times each with 50 ml of aqueous 5% citric acid, once with 50 ml of brine, two times each with 50 ml of aqueous 5% sodium hydrogencarbonate and once with 50 ml of brine, in that order. The resulting organic layer was dried with anhydrous magnesium sulfate and filtered, and the resulting filtrate was concentrated under reduced pressure. The residue was recrystallized from ethyl acetate-hexane to obtain 4.20 g (12.0 mmols, 77.3%) of a solid product of N-t-butoxycarbonyl-D-valine (R)-α-methoxymethylbenzylamide.

60 ml of 4N-HCl/dioxane solution was added to 4.20 g (12.0 mmols) of N-t-butoxycarbonyl-D-valine (R)-α-methoxymethylbenzylamide, and the mixture was stirred at room temperature for one hour. The reaction mixture was concentrated under reduced pressure, 30 ml of ether were added to the residue, and this was again concentrated. The residue was dissolved in 50 ml of methylene chloride, and 1.84 ml (13.2 mmols) of triethylamine and 4.29 g (12.0 mmols) of β-benzyl N-benzyloxycarbonyl-L-aspartate were added thereto. Under cooling, 2.53 g (13.2 mmols) of water-soluble carbodiimide hydrochloride were added thereto, and these were stirred for one hour under cooling and then overnight at room temperature. 150 ml of methylene chloride and 150 ml of ethyl acetate were added to the reaction mixture, which was washed two times each with 50 ml of aqueous 5% citric acid, once with 50 ml of brine, twice each with 50 ml of aqueous 5% sodium hydrogencarbonate solution and once with 50 ml of brine, in that order. The resulting organic layer was dried with anhydrous magnesium sulfate and filtered, and the resulting filtrate was concentrated under reduced pressure. The residue was recrystallized from ethyl acetate-hexane to obtain 6.79 g (11.5 mmols) of N-benzyloxycarbonyl-β-benzyl-L-aspartyl-D-valine (R)-α-methoxymethylbenzylamide as a solid product.

To a suspension of 6.20 g (10.5 mmols) of N-benzyloxycarbonyl-β-benzyl-L-aspartyl-D-valine (R)-α-methoxymethylbenzylamide in 200 ml of methanol and 50 ml of water was added 1.50 g of 10% Pd-carbon (water content 50%). The mixture was reduced under hydrogen under heat at 40° C. The catalyst was removed by filtration, and the resulting filtrate was concentrated under reduced pressure to 15 ml. The crystal thus precipitated was removed by filtration and dried to obtain 2.69 g (7.36 mmols, 70.0%) of α-L-aspartyl-D-valine (R)-α-methoxymethylbenzylamide.

$^1$HNMR (DMSO - d$_6$) δ: 0.84 (d, 3H), 0.88 (d, 3H), 1.90–2.05 (m, 1H), 2.20 (dd, 1H), 2.46 (dd, 1H), 3.23 (s, 3H), 3.45–3.55 (m, 2H), 3.70–3.78 (m, 1H), 4.25 (brs., 1H), 5.04 (q, 1H), 7.20–7.29 (m, 1H), 7.29–7.37 (m, 4H), 8.42 (brs, 1H), 8.52 (d, 1H).

FAB - MS 366 (MH$^+$)

The sweetness potency of the compound was 1300 times that of sugar.

EXAMPLE 12

Production of α-L-aspartyl-D-phenylglycine R-α-methoxymethylbenzylamide:

The same process as in Example 11 was repeated, except that N-t-butoxycarbonyl-D-phenylglycine was used in place of N-t-butoxycarbonyl-D-valine, and α-L-aspartyl-D-phenylglycine (R)-α-methoxymethylbenzylamide was obtained as a solid product. The total yield was 24.4%.

$^1$HNMR (DMSO- d$_6$) δ: 2.22 (dd, 1H), 2.44 (dd, 1H), 3.15 (s, 3H), 3.44 (d, 2H), 3.73 (dd, 1H), 4.99 (q, 1H), 5.59 (s, 1H), 7.23–7.45 (m, 10H), 8.90 (d, 2H).

FAB - MS 400 (MH$^+$)

The sweetness potency of the compound was 500 times that of sugar.

EXAMPLE 13

Production of α-L-aspartyl-α-aminocyclohexanecarboxylic acid (R)-α-methoxymethylbenzylamide:

The same process as in Example 11 was repeated, except that N-t-butoxycarbonyl-α-aminocyclohexanecarboxylic acid was used in place of N-t-butoxycarbonyl-D-valine, and α-L-aspartyl-α-aminocyclohexanecarboxylic acid (R)-α-methoxymethylbenzylamide was obtained as a solid product. The total yield was 81.0%.

$^1$HNMR (DMSO - d$_6$) δ: 1.11–1.73 (m, 8H), 2.05–2.12 (m, 2H), 2.41 (dd, 1H), 2.65 (dd, 1H), 3.24 (s, 3H), 3.48–3.59 (m, 2H), 3.91 (dd, 1H), 4.96 (dd, 1H), 7.19–7.35 (m, 5H), 7.93 (d, 1H), 8.37 (brs, 1H).

FAB - MS 392 (MH$^+$)

The sweetness potency of the compound was 250 times that of sugar.

EXAMPLE 14

Production of α-L-aspartyl-D-valine (S)-α-methoxymethyl-β-methylpropylamide:

The same process as in Example 11 was repeated, except that (S)-α-methoxymethyl-β-methylpropylamine hydrochloride was used in place of (R)-α-methoxymethylbenzylamine hydrochloride, and α-L-aspartyl-D-valine (S)-α-methoxymethyl-β-methylpropylamide was obtained as a solid product. The total yield was 93.6%.

$^1$HNMR (DMSO - d$_6$) δ: 0.83 (d, 3H), 0.85 (d, 6H), 0.88 (d, 3H), 1.76–1.87 (m, 1H), 1.96–2.07 (m, 1H), 2.53 (dd, 1H), 2.67 (dd, 1H), 3.25 (s, 3H), 3.31–3.34, (2dd, 2H), 3.71–3.79 (m, 1H) 4.01 (dd, 1H), 4.35 (dd, 1H), 7.92 (d, 1H), 8.43 (d, 1H).

FAB - MS 332 (MH$^+$)

The sweetness potency of the compound was 40 times that of sugar.

EXAMPLE 15

Production of α-L-aspartyl-D-valine (R)-α-ethoxymethylbenzylamide:

12.5 ml of 4N-HCl/dioxane solution were added to 0.66 g (2.5 mmols) of N-t-butoxycarbonyl-(R)-α-ethoxymethylbenzylamine, and the mixture was stirred at room temperature for one hour. The reaction mixture was concentrated under reduced pressure, 30 ml of ether was added to the residue, and this was further concentrated to obtain (R)-α-ethoxymethylbenzylamine hydrochloride at a quantitative yield.

The thus-obtained (R)-α-ethoxymethylbenzylamine hydrochloride and 1.09 g (2.4 mmols) of N-benzyloxycarbonyl-β-benzyl-L-aspartyl-D-valine were dissolved in 12 ml of methylene chloride, 0.50 g (2.6 mmols) of water-soluble carbodiimide hydrochloride, 0.35 g (2.6 mmols) of HOBt and 0.40 ml (2.7 mmols) of triethylamine were added thereto under cooling, and these were stirred for one hour under cooling and then overnight at room temperature. The reaction mixture was concentrated under reduced pressure, and 50 ml of ethyl acetate was added. The resulting residue was washed two times each with 25 ml of aqueous 5% citric acid, once with 25 ml of brine, two times each with 25 ml of aqueous 5% sodium hydrogencarbonate and once with 25 ml of brine, in that order. The resulting organic layer was dried with anhydrous magnesium sulfate and filtered, and the resulting filtrate was concentrated under reduced pressure. The residue was recrystallized from ethyl acetate-hexane to obtain 1.30 g (2.15 mmols, 89.6%) of a solid product of N-benzyloxycarbonyl-β-benzyl-L-aspartyl-D-valine (R)-α-ethoxymethylbenzylamide.

To a suspension of 1.20 g (1.99 mmols) of N-benzyloxycarbonyl-β-benzyl-L-aspartyl-D-valine (R)-α-ethoxymethylbenzylamide in 50 ml of methanol and 10 ml of water was added 0.30 g of 10% Pd-carbon (water content 50%). The mixture was reduced under hydrogen under heat at 40°C., 40 ml of water was added thereto, the catalyst was removed by filtration, and the resulting filtrate was concentrated under reduced pressure to 5 ml. The crystal thus precipitated was removed by filtration and dried to obtain 0.38 g (1.00 mmol, 50.3%) of α-L-aspartyl-D-valine (R)-α-ethoxymethylbenzylamide.

$^1$HNMR (DMSO- $d_6$) δ: 0.85 (d, 3H), 0.89 (d, 3H), 1.06 (t, 3H), 1.93–2.03 (m, 1H), 2.23 (dd, 1H), 2.46 (dd, 1H), 3.35–3.48 (m, 2H), 3.51 (d, 2H), 3.76 (dd, 1H), 4.26 (brs, 1H), 5.03 (q, 1H), 7.20–7.30 (m, 1H), 7.30–7.38 (m, 4H), 8.43 (brd, 1H), 8.52 (d, 1H).

FAB-MS 380 (MH$^+$)

The sweetness potency of the compound was 500 times that of sugar.

EXAMPLE 16

Production of α-L-aspartyl-D-α-aminobutyric acid (R)-α-methoxymethylbenzylamide:

The same process as in Example 15 was repeated, except that N-benzyloxycarbonyl-β-benzyl-L-aspartyl-D-aminobutyric acid was used in place of N-benzyloxycarbonyl-β-benzyl-L-aspartyl-D-valine and that (R)-α-methoxymethylbenzylamine hydrochloride was used in place of (R)-α-ethoxymethylbenzylamine hydrochloride, and α-L-aspartyl-D-α-aminobutyric acid (R)-α-methoxymethylbenzylamide was obtained as a solid product. The total yield was 56.7%.

$^1$HNMR (DMSO - $d_6$) δ: 0.86 (t, 3H), 1.52–1.75 (m, 2H), 2.22 (dd, 1H), 2.44 (dd, 1H), 3.24 (s, 3H), 3.48–3.51 (2 dd, 2H), 3.64–3.68 (m, 1H), 4.28 (brs, 1H), 4.99–5.06 (m, 1H), 7.24–7.34 (m, 5H), 8.43 (brs, 1H), 8.52 (d, 1H).

FAB-MS 352 (MH$^+$)

The sweetness potency of the compound was 1200 times that of sugar.

EXAMPLE 17

Production of α-L-aspartyl-D-isoleucine (R)-α-methoxymethylbenzylamide:

The same process as in Example 15 was repeated, except that N-benzyloxycarbonyl-β-benzyl-L-aspartyl-D-isoleucine was used in place of N-benzyloxycarbonyl-β-benzyl-L-aspartyl-D-valine and that (R)-α-methoxymethylbenzylamine hydrochloride was used in place of (R)-α-ethoxymethylbenzylamine hydrochloride, and α-L-aspartyl-D-isoleucine (R)-α-methoxymethylbenzylamide was obtained as a solid product. The total yield was 22.1%.

$^1$HNMR (DMSO- $d_6$) δ: 0.84 (t, 3H), 0.88 (d, 3H), 1.01–1.31 (m, 2H), 1.71–1.85 (m, 1H), 2.40 (dd, 1H), 2.57 (dd, 1H), 3.25 (s, 3H), 3.45–3.55 (m, 2H), 3.87 (dd, 1H), 4.31 (brt, 1H), 5.66 (dd, 1H), 7.24–7.38 (m, 5H), 8.49 (brd, 1H), 8.59 (d, 1H).

FAB - MS 380 (MH$^+$)

The sweetness potency of the compound was 500 times that of sugar.

EXAMPLE 18

Production of α-L-aspartyl-D-alanine (R)-α-methoxymethylbenzylamide:

The same process as in Example 15 was repeated, except that N-benzyloxycarbonyl-β-benzyl-L-aspartyl-D-alanine was used in place of N-benzyloxycarbonyl-β-benzyl-L-aspartyl-D-valine and that (R)-α-methoxymethylbenzylamine hydrochloride was used in place of (R)-α-ethoxymethyl benzylamine hydrochloride, and α-L-aspartyl-D-alanine-(R)-α-methoxymethylbenzylamide was obtained as a solid product. The total yield was 57.3%.

$^1$HNMR (DMSO- $d_6$) δ: 1.26 (d, 3H), 2.25 (dd, 1H), 2.46 (dd, 1H), 3.26 (s, 3H), 3.50–3.53 (2d, 2H), 3.61 (q, 1H), 4.31–4.43 (m, 1H), 4.96–5.05 (m, 1H), 7.23–7.39 (m, 5H), 8.35–8.45 (m, 1H), 8.47 (D, 1H).

FAB - MS 338 (MH$^+$)

The sweetness potency of the compound was 300 times that of sugar.

EXAMPLE 19

Production of α-L-aspartyl-D-valine-(R)-α-methoxymethyl-β-methylpropylamide:

The same process as in Example 15 was repeated, except that (R)-α-methoxymethyl-β-methylpropylamine hydrochloride was used in place of (R)-α-ethoxymethylbenzylamine hydrochloride, and α-L-aspartyl-D-valine (R)-α-methoxymethyl-β-methylpropylamide was obtained as a solid product. The total yield was 61.2%.

$^1$HNMR (DMSO - $d_6$) δ: 0.83 (d, 6H), 0.85 (d, 6H), 1.67–1.80 (m, 1H), 1.90–2.22 (m, 1H), 2.22 (dd, 1H), 2.44 (dd, 1H), 3.20 (s, 3H), 3.28 (d, 2H), 3.65–3.80 (m, 2H), 4.20 (brs, 1H), 7.73 (d, 1H), 8.37 (brs, 1H)

FAB - MS 332 (MH$^+$)

The sweetness potency of the compound was 30 times that of sugar.

EXAMPLE 20

Production of α-L-aspartyl-D-valine (S)-α-methoxymethylbenzylamide:

The same process as in Example 15 was repeated, except that (S)-α-methoxymethylbenzylamine hydrochloride was used in place of (R)-α-ethoxymethylbenzylamine hydrochloride, and α-L-aspartyl-D-valine (S)-α-methoxymethylbenzylamide was obtained as a solid product. The total yield was 64.6%.

$^1$HNMR (DMSO - $d_6$) δ: 0.74 (d, 3H), 0.76 (d, 3H), 1.90–2.00 (m, 1H), 2.44 (dd, 1H), 2.58 (dd, 1H), 3.25 (s,

3H), 3.41–3.56 (m, 2H), 3.89–3.96 (m, 1H), 4.33 (brt, 1H), 5.01 (q, 1H), 7.20–7.26 (m, 1H), 7.26–7.33 (m, 4H), 8.45 (d, 1H), 8.65 (d, 1H).

FAB - MS 366 (MH$^+$)

The sweetness potency of the compound was not more than 20 times that of sugar.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An aspartyldipeptide compound or mixture of compounds of the following formula (I) or biologically acceptable salts thereof:

$$\text{L-Asp-X-NH-C*HR}_1\text{R}_2 \qquad (I)$$

wherein $R_1$ represents an alkyl group having from 1 to 6 carbon atoms, or an alkoxymethyl group having from 2 to 7 carbon atoms; $R_2$ represents a phenyl group, a benzyl group, a cyclohexyl group, or a cyclohexylmethyl group, the structure having the C* atom is of an (S) configuration when $R_1$ is an alkyl group and is of an (R) configuration when $R_1$ is an alkoxymethyl group; wherein when $R_1$ is an alkyl group, X represents a residue of a D-α-amino acid or Dl-α-amino acid selected from the group consisting of D-norleucine, D-leucine, D-isoleucine, D-alloisoleucine, D-threonine, D-O-methylthreonine, D-allothreonine, D-O-methylallothreonine, and D- an DL-furylglycine, or a residue of a cyclic or acyclic α,α-dialkylamino acid having from 3 to 6 carbon atoms, but when $R_1$ is an alkoxymethyl group, X represents a residue of a D-α-amino acid or a DL-α-amino acid selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-phenylglycine, and D-and DL-furylglycine, or a residue of a cyclic or acyclic α,α-dialkylamino acid having from 3 to 6 carbon atoms; and the bond between L-Asp and X is an α-bond, and wherein X is not a residue of D-norleucine or D-leucine when $R_1$ represents an alkyl group and $R_2$ represents a phenyl group.

2. The compound or mixture of compounds as claimed in claim 1, wherein X is a residue of D-isoleucine, $R_1$ is an ethyl group, $R_2$ is a phenyl group, and the structure having the C* atom is of an (S) configuration.

3. The compound or mixture of compounds as claimed in claim 1, wherein X is a residue of D-threonine, $R_1$ is an ethyl group, $R_2$ is a phenyl group, and the structure having the C* atom is of an (S) configuration.

4. The compound or mixture of compounds as claimed in claim 1, wherein X is a residue of D- or DL furylglycine, $R_1$ is an ethyl group, $R_2$ is a phenyl group, and the structure having the C* atom is of an (S) configuration.

5. The compound or mixture of compounds as claimed in claim 1, wherein X is a residue of α-aminocyclopentanecarboxylic acid, $R_1$ is an ethyl group, $R_2$ is a phenyl group, and the structure having the C* atom is of an (S) configuration.

6. The compound or mixture of compounds as claimed in claim 1, wherein X is a residue of α-aminocyclohexanecarboxylic acid, $R_1$ is an ethyl group, $R_2$ is a phenyl group, and the structure having the C* atom is of an (S) configuration.

7. The compound or mixture of compounds as claimed in claim 1, wherein X is a residue of D-α-aminobutyric acid, $R_1$ is a methoxymethyl group, $R_2$ is a phenyl group, and the structure having the C* atom is of an (R) configuration.

8. The compound or mixture of compounds as claimed in claim 1, wherein X is a residue of D-valine, $R_1$ is a methoxymethyl group, $R_2$ is a phenyl group, and the structure having the C* atom is of an (R) configuration.

9. The compound or mixture of compounds as claimed in claim 1, wherein X is a residue of D-isoleucine, $R_1$ is a methoxymethyl group, $R_2$ is a phenyl group, and the structure having the C* atom is of an (R) configuration.

10. The compound or mixture of compounds as claimed in claim 1, wherein X is a residue of D-threonine, $R_1$ is a methoxymethyl group, $R_2$ is a phenyl group, and the structure having the C* atom is of an (R) configuration.

11. The compound or mixture of compounds as claimed in claim 1, wherein X is a residue of D-α-phenylglycine, $R_1$ is a methoxymethyl group, $R_2$ is a phenyl group, and the structure having the C* atom is of an (R) configuration.

12. The compound or mixture of compounds as claimed in claim 1, wherein X is a residue of α-aminocyclohexanecarboxylic acid, $R_1$ is a methoxyethyl group, $R_2$ is a phenyl group, and the structure having the C* atom is of an (R) configuration.

13. The compound or mixture of compounds as claimed in claim 1, wherein X is a residue of D-valine, $R_1$ is an ethoxymethyl group, $R_2$ is a phenyl group, and the structure having the C* atom is of an (R) configuration.

14. The compound or mixture of compounds as claimed in claim 1, wherein X is a residue of D- or DL-furylglycine, $R_1$ is a methoxymethyl group, $R_2$ is a phenyl group, and the structure having the C* atom is of an (R) configuration.

15. A sweetener composition, comprising an effective sweetening amount of the aspartyldipeptide compound of claim 1, or its biologically acceptable salt.

16. The compound or compounds as claimed in claim 1, wherein $R_1$ is methoxymethyl.

17. A sweetener composition comprising an effective sweetening amount of the aspartyldipeptide compound of claim 16, or its biologically acceptable salt.

* * * * *